United States Patent [19]
Sonoi et al.

[11] Patent Number: 5,998,564
[45] Date of Patent: Dec. 7, 1999

[54] PROCESS FOR PRODUCING BISTHIOPHENOLPERFLUOROALKYLIDENE COMPOUND

[75] Inventors: Takehiro Sonoi, Kitaibaraki; Haruyoshi Tatsu, Hitachi; Satoru Saito, Kitaibaraki, all of Japan; Sergei Rafailovich Sterlin, Moscow, Russian Federation; Victor Filippovich Cherstokov, Moscow, Russian Federation; Nina Ivanovna Delyagina, Moscow, Russian Federation

[73] Assignee: Nippon Mektron, Limited, Tokyo, Japan

[21] Appl. No.: 09/235,966

[22] Filed: Jan. 22, 1999

Related U.S. Application Data

[60] Continuation of application No. 09/006,717, Jan. 14, 1998, which is a division of application No. 08/675,603, Jul. 3, 1996, Pat. No. 5,891,964.

[30] Foreign Application Priority Data

Jul. 7, 1995 [JP] Japan .................................. 7-196108

[51] Int. Cl.$^6$ ...................................................... C08G 75/02
[52] U.S. Cl. ....................... 528/174; 525/326.3; 525/350; 528/374; 528/376
[58] Field of Search ..................................... 528/174, 374, 528/375, 376; 568/65; 525/326.3, 350

[56] References Cited

U.S. PATENT DOCUMENTS

| | | | |
|---|---|---|---|
| 4,062,830 | 12/1977 | Ceccato | 525/326.3 |
| 4,259,463 | 3/1981 | Moggi | 525/326.3 |
| 4,562,243 | 12/1985 | Percec | 528/174 |
| 4,720,590 | 1/1988 | Giants | 568/65 |

*Primary Examiner*—Gary Geist
*Assistant Examiner*—Jean F Vollano
*Attorney, Agent, or Firm*—Barnes & Thornburg

[57] ABSTRACT

2.2'-bis(3-mercaptophenyl)hexafluoropropane [bisthiophenol AF] is obtained in good yield by chlorosulfonating 2.2'-bisphenylhexafluoropropane and reducing the thus quantitatively obtained 2,2'-bis(3-chlorosulfonylphenyl)-hexafluoropropane with zinc under acidic conditions and is effectively used as a cross-linking agent for a fluorine-containing elastomer having halogenophenyl groups as cross-linkable groups.

2 Claims, No Drawings

PROCESS FOR PRODUCING BISTHIOPHENOLPERFLUOROALKYLIDENE COMPOUND

This is a Continuation of Application Ser. No. 09/006,717, filed Jan. 14, 1998, which is a divisional application of Application Ser. No. 08/675,603, filed Jul. 3, 1996 now U.S. Pat. No. 5,891,964.

BACKGROUND OF THE INVENTION

1. Field of the Invention

The present invention relates to a process for producing a bisthiophenolperfluoroalkylidene compound, and more particularly to a process for producing a bisthiophenol- perfluoroalkylidene compound effectively applicable as a precursor for synthesis of polysulfide or as a cross-linking agent for fluorine-containing polymers.

2. Related Prior Art

U.S. Pat. No. 4,720,590 discloses that 2,2-bis(mercapto-phenyl)hexafluoropropane [2, 2, 2-trifluoro-1-(trifluoromethyl)-ethylidene-bisbenzenethiol] represented by the following formula:

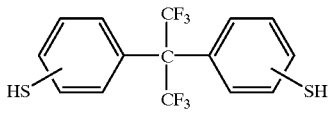

can be effectively used as a precursor for synthesis of polysulfide.

In such a compound, the SH group can take the m- or p-position. The m-substituted compound can be obtained from 2,2'-bisphenylhexafluoropropane as a starting material through total 7 synthesis steps, and the yield through the total 7 steps is not definitely disclosed therein because of incomplete disclosure of indivisual step yields, and seems not to exceed about 50%. Thus, it seems that the desired compound is not obtained in good yield.

SUMMARY OF THE INVENTION

An object of the present invention is to provide a process for producing a bisthiophenolperfluoroalkylidene compound in good yield from a bisphenylperfluoroalkylidene compound such as 2,2'-bisphenylhexafluoropropane, etc. as a starting material.

According to the present invention, a bis(chlorosulfonyl-phenyl)perfluoroalkylidene compound represented by the following general formula [I]:

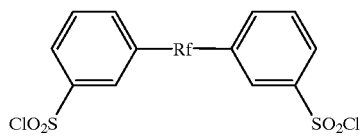

wherein Rf is a perfluoroalkylidene group having 1 to 10 carbon atoms, is reduced with zinc under acidic conditions to produce a bisthiophenolperfluoroalkylidene compound represented by the following general formula [II]:

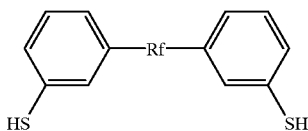

wherein Rf has the same meaning as defined above.

DETAILED DESCRIPTION OF THE INVENTION

In the general formula [I], a perfluoroisopropylidene group is usually used as a perfluoroalkylidene group having 1 to 10 carbon atoms, and thus description will be made below particularly of a process for producing 2,2'-bis(3-chloro-sulfonyl)hexafluoropropane shown by the following formula:

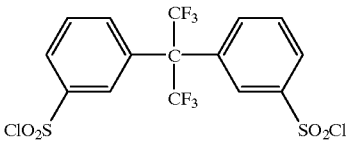

2,2'-bisphenylhexafluoropropane as a starting material is dropwise added to chlorosulfonic acid in excess moles at a temperature of about 0 to about 20° C. with stirring and heated, after the dropwise addition, at a temperature of about 40 to about 100° C., preferably about 50 to about 70° C., for about 1 to about 24 hours, whereby 2,2'-bis(3-chlorosulfonylphenyl)hexa-fluoropropane can be obtained substantially quantitatively. The thus obtained 2,2'-bis(3-chlorosulfonylphenyl)hexafluoro-propane is a novel compound.

This compound is dissolved in a solvent, preferably an aromatic hydrocarbon such as benzene, toluene, etc. and then admixed with zinc dust in excess moles, and the resulting mixture is subjected to reaction under acidic conditions formed, for example, by dropwise addition of concentrated hydrochloric acid thereto. After the dropwise addition, the mixture is stirred at a temperature of not more than about 40° C., preferably not more than about 20° C. for about 1. to about 10 hours, preferably about 1 to about 3 hours, and then heated at a temperature of about 50 to about 100° C., preferably about 60 to about 70° C. for about 1 to about 10 hours, preferably about 2 to about 3 hours, whereby reduction reaction of chlorosulfonyl groups to mercapto groups can be completed in yield of about 60% or more. The reaction product 2,2'-bis(3-mercaptophenyl) hexafluoropropane can serve not only as a precursor for synthesis of polysulfide, as disclosed in the above-mentioned US patent, but it was newly found that the reaction product was effectively applicable as a cross-linking agent for a fluorine-containing elastomer having halogenophenyl groups as cross-linkable groups.

As a fluorine-containing elastomer having halogenophenyl groups as cross-linkable groups, generally a terpolymer comprising about 30 to about 70% by mole of tetrafluoroethylene, about 65 to about 25% by mole of perfluoro(lower alkyl vinyl ether) or perfluoro(lower alkoxy-lower alkyl vinyl ether) and about 0.1 to about 5% by mole of a halogeno-phenyl-containing vinyl ether compound, sum total being 100% by mole, is used.

As a perfluoro(lower alkyl vinyl ether), generally perfluoro(methyl vinyl ether) is used.

As a perfluoro(lower alkoxy-lower alkyl vinyl ether), for example, the following compounds are used:

| | |
|---|---|
| $CF_2 = CFOCF_2CF(CF_3)OC_nF_{2n+1}$ | (n: 1 to 5) |
| $CF_2 = CFO(CF_2)_3OC_nF_{2n+1}$ | (n: 1 to 5) |
| $CF_2 = CFOC_2CF(CF_3)O(CF_2O)_nC_nF_{2n+1}$ | (n: 1 to 5, m: 1 to 3) |
| $CF_2 = CFO(CF_2)_2OC_nF_{2n+1}$ | (n: 1 to 5) |

Among them, preferably the compounds having $CF_3$ group as $C_nF_{2n+1}$ group are used.

As a halogenophenyl-containing vinyl ether compound serving as a cross-linking site monomer, the following compound is used:

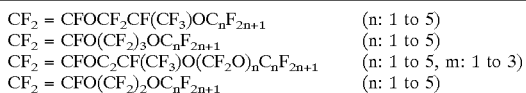

wherein X is a halogen atom and n is an integer of 1 to 5.

Such a vinyl ether compound can be obtained by subjecting $CF_2=CFO(CF_2)nCOOR$ to addition reaction of chlorine or bromine (Y), then subjecting the resulting $CF_2YCFYO(CF_2)nCOOR$ to hydrolysis and acid chloridizing reaction, and then subjecting the resulting product to reaction with monohalogeno-benzene and then to reaction with $SF_4$ to convert —CO— to —$CF_2$—, followed by dechlorination reaction or debromination reaction, or by subjecting $CF_2=CFO(CF_2)nCOOR$ to hydrolysis and acid chloridizing reaction, and subjecting the resulting product to reaction with monohalogenobenzene and then to reaction with $SF_4$ to convert —CO— to —$CF_2$—.

The terpolymer, comprising the above-mentioned three components as essential components can be further copolymerized with fluoroolefins, olefins, vinyl compounds, etc. to such a degree as not to inhibit the copolymerization reaction and not to deteriorate properties of vulcanization products (for example, not more than about 20% by mole).

Bisthiophenolperfluoroalkylidene compound can be produced in good yield by reducing a bis(chlorosulfonylphenyl)perfluoroalkylidene compound as a novel compound. The bisthiophenol-perfluoroalkylidene compound or its alkali metal salt can be effectively used as a cross-linking agent for a fluorine-containing elastomer having halogenophenyl groups as cross-linkable groups.

PREFERRED EMBODIMENTS OF THE INVENTION

The present invention will be described in detail below, referring to Examples.

EXAMPLE 1

27 g (0.09 moles) of 2.2'-bisphenylhexafluoropropane was dropwise added to 85 g (0.73 moles) of chlorosulfonic acid charged into a reactor vessel at 10 to 12° C. with stirring over 15 minutes. After the dropwise addition, the mixture was heated at 50° C. for 3 hours, and then poured into ice water, and the solid residue was recovered therefrom by filtration, whereby 2,2'-bis(3-chlorosulfonylphenyl) hexafluoropropane having the following characteristics was obtained substantially quantitatively:

MS: 500 $[M]^+10$
465 $[M-Cl]^+100$
401 $[M-SO_2Cl]^+10$
337 $[C_{15}H_8ClF_5]^+50$
302 $[M-2SO_2Cl]^+40$
233 $[M-CF_3-2SO_2Cl]^+90$

EXAMPLE 2

A mixture consisting of 50 g (0.1 mole) of 2,2'-bis(3-chlorosulfonylphenyl)hexafluoropropane dissolved in 180 ml of benzene and 96.5 g (1.48 moles) of zinc dust was charged into a reactor vessel and then 380 ml of concentrated hydrochloric acid was dropwised added thereto with stirring, while keeping the reaction mixture at a temperature not higher than 20° C. Then, the reaction mixture was heated at 20° C. for 2 hours, and then at 60 to 70° C. for 3 hours and then cooled down to room temperature, and the reaction product was extracted into benzene. The extract was washed with 300 ml of a degasified aqueous solution containing 0.05 g of $Na_2S_2O_4$ and then the benzene was distilled off, whereby 22.95 g of 2,2'-bis(3-mercaptophenyl) hexafluoropropane [bisthiophenol AF] having the following characteristics was obtained (yield: 62.3%):

MS: 732 [A]
734[B]
368$[MN]^+100$
334 $[M-H_2S]^+20$
299$[M-CF_3-HS]^+25$
233$[M-CF_3-H_2S]^+80$
Purity: 83% (according to iodine oxidation titrimetry)
Elemental analysis:
Found: C 48.96%, H 2.70%, F 31.09%
Calculated: C 48.91%, H 2.72%, F 30.98%
Note: A seems to be a molecular ion of bis-thiol type shown by the following formula:

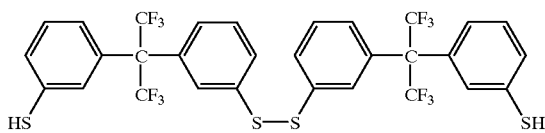

B seems to be a molecular ion of bis-disulfide type shown by the following formula:

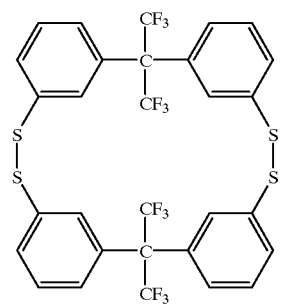

EXAMPLE 3

Added to 100 parts by weight of terpolymer of tetrafluoro-ethylene-perfluoro(methyl vinyl ether)-4-(4'-fluorophenyl)-perfluoro(butyl vinyl ether) (molar ratio 63.2:35.3:1.5) [reduced viscosity of 1 wt. % solution in perfluoro(2-butyl-tetrahydrofuran), measured at 35° C., nsp/c: 1.86 ml/g] were:

|                                      | Parts by weight |
|--------------------------------------|-----------------|
| MT carbon black                      | 20              |
| Bisthiophenol AF dipotassium salt    | 3               |
| Benzyltriphenylphosphonium chloride  | 1               |
| Magnesium oxide                      | 4               | and the mixture was kneaded through a double roll rubber mill. The kneaded mixture was subjected to press vulcanization (primary vulcanization) at 180° C. for 30 minutes and then to oven vulcanization (secondary vulcanization) in a nitrogen gas atmosphere according to the following heating schedule. It was observed that the vulcanization torque was increased even in the primary vulcanization, and progress of vulcanization was confirmed.

Heating schedule:
1) Heating at 90° C. for 4 hours,
2) Elevating the temperature from 90° C. to 204° C. over 6 hours,
3) Heating at 204° C. for 18 hours,
4) Elevating the temperature from 204° C. to 288° C. over 6 hours, and
5) Heating at 288° C. for 18 hours.

Compression sets at 200° C. and 250° C. of the thus obtained vulcanization product were measured and found to be 66% and 68%, respectively.

The terpolymer of tetrafluoroethylene-perfluoro(methyl vinyl ether)-4-(4'-fluorophenyl)-perfluoro(butyl vinyl ether) used in this Example was prepared in the following manner:

1.8 liters of distilled water, 23.7 g of ammonium perfluorooctanoate, 14.3 g of $Na_2HPO_4.12H_2O$ and 0.67 g of $NaH_2PO_4.2H_2O$ were charged into a stainless steel autoclave having a capacity of 3 liters and then the autoclave inside gas was replaced with a nitrogen gas, followed by pressure reduction of the autoclave.

Then, 25 g of tetrafluoroethylene, 55 g of perfluoro (methyl vinyl ether) and 7.2 g of 4- (4'-fluorophenyl)-perfluoro (butyl vinyl ether) were successively charged into the autoclave, and after elevation of the autoclave temperature to 50° C., 1.66 g of sodium sulfite and 9.08 g of ammonium persulfate, each in the form of 50 ml of aqueous solutions, were added thereto to initiate polymerization reaction.

In the course of polymerization reaction, tetrafluoroethylene was additionally supplied thereto at a rate of 12.8 g/hr, perfluoro (methyl vinyl ether) at a rate of 16.5 g/hr and 4-(4'-fluorophenyl)-perfluoro(butyl vinyl ether) at a rate of 2.2 g/hr to keep the autoclave inside pressure at 9 kg/cm² gage. 19 hours after the initiation of polymerization reaction, the additional supply was discontinued, and the reaction mixture was kept, as it was, for one hour. Then, the autoclave was cooled and the remaining gas was purged therefrom. An aqueous latex having a solid concentration of 20 wt. % was taken out of the autoclave.

Then, the aqueous latex was added to 20 liters of an aqueous saturated sodium chloride solution at 70° C. to coagulate the resulting polymer. The coagulate was recovered by filtration, washed with water and dried at 70° C. under the atmospheric pressure for 12 hours and then at 120° C. under reduced pressure for 12 hours, whereby 560 g of white rubbery terpolymer was obtained. It was found by infrared absorption spectra that the terpolymer had absorptions at 1520 $cm^{-1}$ and 1615 $cm^{-1}$, and copolymerization of perfluoro[4-(4'-fluorophenyl) butyl vinyl ether] into the terpolymer was confirmed thereby.

EXAMPLE 4

Added to 100 parts by weight of terpolymer of tetrafluoro-ethylene-perfluoro(methyl vinyl ether)-4-(4'-chlorophenyl)-perfluoro(butyl vinyl ether) (molar ratio 72.8:25.7:1.5) [reduced viscosity of 1 wt.% solution in perfluoro(2-butyl-tetrahydrofuran), measured at 35° C., ηsp/c: 1.80 ml/g] were:

|                                      | Parts by weight |
|--------------------------------------|-----------------|
| MT carbon black                      | 20              |
| Bisthiophenol AF dipotassium salt    | 3               |
| Benzyltriphenylphosphonium chloride  | 1               |
| Magnesium oxide                      | 4               | and the mixture was kneaded through a double roll rubber mill. The kneaded mixture was subjected to press vulcanization (primary vulcanization) at 180° C. for 30 minutes and then to oven vulcanization (secondary vulcanization) in a nitrogen gas atmosphere according to the following heating schedule. It was observed that the vulcanization torque was increased even in the primary vulcanization, and progress of vulcanization was confirmed.

Heating schedule:
1) Heating at 90° C. for 4 hours,
2) Elevating the temperature from 90° C. to 204° C. over 6 hours,
3) Heating at 204° C. for 18 hours,
4) Elevating the temperature from 204° C. to 288° C. over 6 hours, and
5) Heating at 288° C. for 18 hours.

Compression sets at 200° C. and 250° C. of the thus obtained vulcanization product were measured and found to be 48% and 57%, respectively.

The terpolymer of tetrafluoroethylene-perfluoro(methyl vinyl ether)-4-(4'-chlorophenyl)-perfluoro(butyl vinyl ether) used in this Example was prepared in the following manner:

1.7 liters of distilled water, 54.6 g of ammonium perfluorooctanoate and 23.7 g of $KH_2PO_4.2H_2O$ were charged into a stainless steel autoclave having a capacity of 3 liters and then the autoclave inside gas was replaced with a nitrogen gas, followed by pressure reduction of the autoclave.

Then, 31 g of tetrafluoroethylene, 45 g of perfluoro (methyl vinyl ether) and 5.6 g of 4-(4'-chlorophenyl)-perfluoro(butyl vinyl ether) were successively charged into the autoclave, and after elevation of the autoclave temperature to 60° C., 0.18 g of sodium sulfite and 1.0 g of ammonium persulfate, each in the form of 50 ml of aqueous solutions, were added thereto to initiate the polymerization reaction.

In the course of polymerization reaction, tetrafluoroethylene was additionally supplied thereto at a rate of 9.6 g/hr, perfluoro(methyl vinyl ether) at a rate of 9.6 g/hr and 4-(4'-chlorophenyl)-perfluoro(butyl vinyl ether) at a rate of 0.94 g/hr to keep the autoclave inside pressure at 9 kg/cm² gage.At the time of 5 hours 6 minutes after the initiation of polymerization reaction, the additional supply was discontinued, and the reaction mixture was kept, as it was, for one hour. Then, the autoclave was cooled and the remaining gas was purged therefrom. An aqueous latex having a solid concentration of 10.6 wt.% was taken out of the autoclave.

Then, the aqueous latex was added to 20 liters of an aqueous saturated sodium chloride solution at 70° C. to coagulate the resulting polymer. The coagulate was recovered by filtration, washed with water and dried at 70° C.

under the atmospheric pressure for 12 hours and then at 120° C. under reduced pressure for 12 hours, whereby 125 g of white rubbery terpolymer was obtained. It was found by infrared absorption spectra that the terpolymer had absorptions at 1490 cm$^{-1}$ and 1600 cm$^{-1}$, and copolymerization of perfluoro[4-(4'-chlorophenyl) butyl vinyl ether] into the terpolymer was confirmed thereby.

What is claimed is:

1. A method of cross-linking a fluorine-containing elastomer which comprises:

providing a fluorine-containing elastomer having halogenophenyl groups as cross-linkable groups;

providing a cross-linking agent which comprises a bisthiophenolperfluoroalkylidene compound represented by the following general formula:

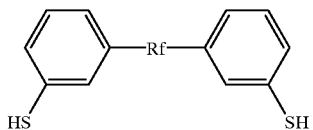

where Rf is a perfluoroalkylidene group having 1 to 10 carbon atoms, or its alkali metal salt; and contacting the fluorine-containing elastomer having halogenophenyl groups as cross-linkable groups with the cross-linking agent to effect cross-linking of the fluorine-containing elastomer, wherein the fluorine-containing elastomer having halogenophenyl groups as cross-linkable groups is a terpolymer comprising about 30 to about 70 mole percent of tetrafluoroethylene, about 56 to about 24 mole percent of perfluoro(lower alkyl vinyl ether) or perfluoro(lower alkoxy-lower alkyl vinyl ether) and about 0.1 to about 5 mole percent of a halogenophenyl-containing vinyl ether compound.

2. A method of cross-linking a fluorine-containing elastomer according to claim 1, wherein the halogenophenyl-containing vinyl ether compound is a vinyl ether compound represented by the following general formula:

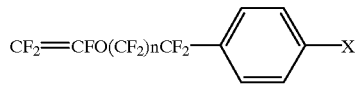

wherein X is a halogen atom and n is an integer of 1 to 5.

* * * * *